US005674485A

United States Patent [19]

Hammock et al.

[11] Patent Number: 5,674,485
[45] Date of Patent: Oct. 7, 1997

[54] INSECT DIAGNOSTIC AND CONTROL COMPOSITIONS WITH TRUNCATED JHE

[75] Inventors: Bruce D. Hammock, Davis; Linda M. Reilly, Fremont, both of Calif.

[73] Assignee: The Regents of the University of California, Oakland, Calif.

[21] Appl. No.: 453,323

[22] Filed: May 30, 1995

Related U.S. Application Data

[63] Continuation-in-part of Ser. No. 927,851, Aug. 10, 1992, abandoned, which is a continuation-in-part of Ser. No. 725,226, Jun. 26, 1991, abandoned, which is a continuation of Ser. No. 265,507, Nov. 1, 1988.

[51] Int. Cl.$^6$ .......................... A01N 63/00; C12N 15/85
[52] U.S. Cl. .................... 424/93.2; 435/172.3; 435/196; 435/320.1; 435/348; 536/23.2; 536/23.5
[58] Field of Search .................... 435/172.1, 172.3, 435/320.1, 69.8, 69.1, 183, 196; 424/93.2, 93.6; 536/23.2, 23.5

[56] References Cited

U.S. PATENT DOCUMENTS

| | | | |
|---|---|---|---|
| 4,668,511 | 5/1987 | Aspirot et al. | 424/93.6 |
| 4,745,051 | 5/1988 | Smith et al. | 435/69.51 |
| 4,762,547 | 8/1988 | Iwasaki et al. | 504/330 |
| 4,870,023 | 9/1989 | Fraser et al. | 435/235.1 |
| 4,888,340 | 12/1989 | Neh et al. | 514/403 |
| 4,929,718 | 5/1990 | Possani et al. | 530/320 |
| 5,071,748 | 12/1991 | Miller | 435/69.1 |
| 5,098,706 | 3/1992 | Hammock et al. | 424/93 A |
| 5,162,308 | 11/1992 | Brown et al. | 514/63 |
| 5,177,308 | 1/1993 | Barton et al. | 800/205 |
| 5,180,581 | 1/1993 | Miller et al. | 424/93.2 |
| 5,238,724 | 8/1993 | Bjostad, III et al. | 424/84 |
| 5,266,314 | 11/1993 | Maeda | 424/93.2 |
| 5,266,317 | 11/1993 | Tomalski et al. | 424/93.2 |

FOREIGN PATENT DOCUMENTS

| | | |
|---|---|---|
| 0222412B | 11/1986 | European Pat. Off. |
| 0225777A | 12/1986 | European Pat. Off. |
| 2074868 | 3/1981 | United Kingdom |

OTHER PUBLICATIONS

Hammock et al., "The Role of Juvenile Hormone Metabolism in the Metamorphosis of Selected Lepidoptera," *Chemical Abstracts*, 102 (1985), entry 76006b.

Abdel–Aal and Hammock, "3–Octylthio–1,1,1–trifluoro–2–propanone, A High Affinity and Slow Binding Inhibitor of Juvenile Hormone Esterase from *Trichoplusia ni* (Hüber)," *Insect Biochem.*, 15:1 (1985), pp. 111–122.

Abdel–Aal and Hammock, "Transition State Analogs as Ligands for Affinity Purification of Juvenile Hormone Esterase," *Science*, 233 (Sep. 1986), pp. 1073–1076.

Bachmair and Varshavsky, "The Degradation Signal in a Short–Lived Protein," *Cell*, 56 (Mar. 1989), pp. 1019–1032.

Cheung and Hammock, "Micro–Lipid–Droplet Encapsulation of *Bacillus thuringiensis* subsp. *israelensis* δ–Endotoxin for Control of Mosquito Larvae," *Appl. & Environ. Microbiol.*, 50:4 (Oct. 1985), pp. 984–988.

Chiang and Dice, "Peptide Sequences that Target Proteins for Enhanced Degradation During Serum Withdrawal," *J. of Biol. Chem.*, 263:14 (May 1988), pp. 6797–6805.

Hammock and Sparks, "A Rapid Assay for Insect Juvenile Hormone Esterase Activity," *Analytical Biochemistry*, 82 (1977), pp. 573–579.

Hammock et al., "Expression and Effects of the Juvenile Hormone Esterase in a Baculovirus Vector," *Nature*, 344:6265 (Mar. 1990), pp. 458–461.

Hammock and Rose, "Analysis of Juvenile Hormone Esterase Activity," Chpt. 32, pp. 487–495 in Law et al. (Eds.), *Methods in Enzymology*, vol. III: *Steroids and Isoprenoids* (Part B), Academic Press (1985).

Hammock et al., "Trifluoromethylketones as Possible Transition State Analog Inhibitors of Juvenile Hormone Esterase," *Pesticide Biochem. & Physiology*, 17 (1982), pp. 76–88.

Hammock et al., "Selective Inhibition of JH Esterases from Cockroach Hemolymph," *Pesticide Biochem. & Physiology*, 7 (1977), pp. 517–530.

Hammock et al., "Strategies for the Discovery of Insect Control Agents: . . . " Chpt. 12 in Steffens et al. (Eds), *Biomechanism Regulating Growth & Development*, USDA Beltsville Symp. vol. 12, Kluwer Academic Press (1988).

Hanzlik et al., "Isolation and Sequencing of cDNA Clones Coding for Juvenile Hormone Esterase from *Heliothis virescens*," *J. of Biol. Chem.*, 264:21 (Jul. 1989), pp. 12419–12425.

Hanzlik and Hammock, "Characterization of Affinity–purified Juvenile Hormone Esterase from *Trichoplusia ni*," *J. Biol. Chem.*, 1987:23 (Oct. 1987), pp. 12584–13591.

Huynh et al., "Constructing and Screening cDNA Libraries in λgt10 and λgt11," Chpt. 2, IRL Press (Oxford), (1985), pp. 49–78.

(List continued on next page.)

*Primary Examiner*—John L. LeGuyader
*Attorney, Agent, or Firm*—Majestic, Parsons, Siebert & Hsue

[57] ABSTRACT

A recombinant expression vector is provided that is capable of expression in a host insect and includes a coding sequence for juvenile hormone esterase that, when expressed, lacks the signal sequence targeting the enzyme to the plasma membrane, and thus the resulting protein is cytoplasmic and non-glycosylated. Recombinant microbe embodiments have improved insecticidal activity because the modified, or truncated, protein builds up in microbe-infected cells within the insect and reduces the time taken for the microbe to kill the host.

12 Claims, 3 Drawing Sheets

OTHER PUBLICATIONS

Ichinose et al., "Pharmacokinetic Studies of the Recombinant Juvenile Hormone Esterase in *Manduca sexta*", *Pesticide Biochem. & Physiology*, 42 (1992), pp. 13–23.

Ichinose et al., "Uptake of Juvenile Hormone Esterase by Pericardial Cells of *Manduca sexta*," submitted to *Insect Biochem. Molec. Biol.* (1992).

McCutchen et al., "Development of a Recombinant Baculovirus Expressing an Insect-Selective Neurotoxin: Potential for Pest Control," *Bio/Technology*, 9 (Sep. 1991), pp. 848–852.

Philpott and Hammock, "Juvenile Hormone Esterase is a Biochemical Anti-Juvenile Hormone Agent," *Insect Biochem.*, 20:5 (1990), pp. 451–459.

Rogers et al., "Amino Acid Sequences Common to Rapidly Degraded Proteins: The PEST Hypothesis," *Science*, 234 (Oct. 1986), pp. 364–368.

Sparks and Hammock, "Induction and Regulation of Juvenile Hormone Esterases During the Last Larval Instar of the Cabbage Looper, *Trichoplusia ni*," *J. Insect. Physiolo.*, 25 (1979), pp. 551–560.

Sparks and Hammock, "Comparative Inhibition of the Juvenile Hormone Esterases from *Trichoplusia ni, Tenebrio molitor*, and *Musca domestica*," *Pesticide Biochem. & Physiology*, 14 (1980), pp. 290–302.

Wozniak and Jones, "Immunochemical Characterization of Juvenile Hormone Esterase from Different Species of Lepidoptera," *Biochem. & Biophys. Res. Commun.*, 144:3 (May 1987), pp. 1281–1286.

Wroblewski et al., "Regulation of Juvenile Hormone Esterase Gene Expression in the Tobacco Budworm (*Heliothis virescens*)," *Archives of Biochem. & Biophys.*, 278:2 (May 1990), pp. 461–466.

Eldridge et al., "Insecticidal Properties of Genetically Engineered Baculoviruses Expressing an Insect Juvenile Hormone Esterase Gene," *Appl. & Environ. Microbiol.*, 58:5 (May 1992), pp. 1583–1591.

Hayakawa, "Structure of a Growth-Blocking Peptide Present in Parasitized Insect Hemolymph," *J. of Biol. Chem.*, 266:13 (May 5, 1991), pp. 7982–7984.

Hayakawa, "A Putative New Juvenile Peptide Hormone in Lepidopteran Insects," *Biochemical and Biophysical Research Communications*, 185:3 (Jun. 30, 1993), pp. 1141–1147.

Smith et al., "Production of Human Beta Interferon in Insect Cells Infected with a Baculovirus Expression Vector," *Mol. Cell Biol.*, 3 (1983), pp. 2156–2165.

Betana et al., "Potential of Baculo Viruses Expressing a Scorpion Toxin and an Esterase in Agriculture . . . ." *Abstr. Pap. Am. Chem. Soc.*, (206 Meet., Pt. 1, AGR0122), 1993 (Abstract only).

Hayakawa, "Juvenile Hormone Esterase Activity Repressive Factor in the Plasma of Parasitized Insect Larvae," *J. Biol. Chem.*, 265:19 (1990), pp. 10812–10816.

Hayakawa, "Juvenile Hormone Esterase Activity Repressive Peptide in the Parasitized Armyworm Hemolymph," *Zool. Sci.* (Tokyo), 7:6 (1990), p. 1061 (Abstract only).

Ward et al., "Analaysis of the Catalytic Mechanism of Juvenile Hormone Esterase by Site-Directed Mutagenesis," *Int. J. Biochem.* (England), 24:12 (Dec. 1993), pp. 1933–1941 (Abstract only).

Hammock et al., "Development of Recombinant Viral Insecticides by Expression of an Insect-Speicfic Toxin . . . ." *Arch. Insect Biochem. Physiol.* (US), 22:3–4 (1993), pp. 315–344 (Abstract only).

Possee et al., "Expression of the Proteins with Insecticidal Activities Using Baculo Virus Vectors . . . ." *Ann. N.Y. Acad. Sci.*, 646 (1991), pp. 234–239 (Abstract only).

Hammock et al., "Improving the Efficacy of Baculo Virus Insecticides by Expressing with Insect Selective Proteins," *Abstr. Pap. Am. Chem. Soc.* (202 Meet., Pt. 1, AGR09) (1991) (Abstract only).

Bonning et al., "Further Development of a Recombinant Baculovirus Insecticide Expressing the Enzyme JHE from *Heliothis-Virescens,*" *Biochem. Mol. Biol.*, 22:5 (1992) pp. 453–458 (Abstract only).

Piek et al., "The Pharmacology of Microbracon Venom," *Comp. Biochem. Physiol.*, vol. 72C, pp. 303–309 (1982).

Miller et al., "Bacterial, Viral, and Fungal Insecticides," *Science*, 219, pp. 715–721, (Feb. 11, 1983).

Sakurai et al., "Complete Nucleotide Sequence of Gene for Sex-Specific Storage Protein of *Bombyx mori,*" *Nucleic Acids Research*, 16:15, pp. 7717–7718 (1988).

Merryweather et al., "Construction of Genetically Engineered Baculovirus Insecticides Containing the *Bacillus thuringiensis* subsp. *kurstaki* HD-73 Delta Endotoxin," *J. of Gen. Virol.*, 71, pp. 1535–1544 (1990).

Martens et al., "Insecticidal Activity of a Bacterial Crystal Protein Expressed by a Recombinant Baculovirus in Insect Cells," *Applied and Envrionmental Microbiology*, 56:9 pp. 2764–2770, (Sep. 1990).

Tomalski and Miller, "Insect Paralysis by Baculovirus-Mediated Expression of a Mite Neurotoxin Gene," *Nature*, 352, pp. 82–85, (Jul. 4, 1991).

Zlotkin, "Toxins Derived from Arthropod Venoms Specifically Affecting Insects," Chpt. 15 in *Comprehensive Insect Physiology, Biochemistry & Pharmacology*, vol. 10, pp. 499–541 (1985).

Gordon et al., "The Binding of the insect Selective Neurotoxin (AaIT) from Scorpion Venom to Locust Synaptosomal Membranes," *Biochimica et Biophysica Acta*, 778, pp. 349–358 (1984).

Stewart et al., "Construction of an Improved Baculovirus Insecticide Containing an Insect-Specific Toxin Gene," *Nature*, 352, pp. 85–88, (Jul. 4, 1991).

McCutchen et al., "Development of Surrogate Substrates for Juvenile Hormone Esterase," *Archives of Biochemistry and Biophysics*, 307:2 (Dec. 1993), pp. 231–241.

Abdel-Aal and Hammock, "Apparent Multiple Catalytic Sites Involved in the Ester Hydroysis of Juvenile Hormones by the Hemolymph and . . . ." *Arch. Biochem. Biophys.*, 243:1, (1985), pp. 206–219.

Maeda et al., "Insecticidal Effects of an Insect-Specific Neurotoxin Expressed by a Recombinant Baculovirus," *Virology*, 184 (1991), pp. 777–780.

Touhara et al., "Ligand Binding by a Recombinant Insect Juvenile Hormone Binding Protein," *Biochem.*, 32:8 (1993), pp. 2068–2075.

McCutchen et al., "Recombinant Baculovirus Expressing an Insect-selective Neurotoxin: . . . ." in *Natural & Engineered Pest Management Agents* (Hedin et al., eds), ACS Sympo. Series #551, Am. Chem. Soc., (1994) pp. 348–367.

Heinz et al., "Direct Effects of Recombinant Nuclear Polyhedrosis Viruses on Selected Non-Target Organisms," *J. Econ. Entomol.*, 88:2, (1995), pp. 259–264.

Hammock, "Recombinant Baculoviruses as Biological Insecticides," in *Pest Management: Biolgoiclly Based Technologies* (Lumsden and Vaughn, eds.), ACS Symp. Series, Am. Chem. Soc., (1993), pp. 313–325.

Bonning and Hammock, "Lethal Ratios: An Optimized Strategy for Presentation of Bioassay Data Generated from Genetically Engineered Baculoviruses," *J. Invert. Pathol.*, 62 (1993), pp. 196–197.

Maeda et al., "Recombinant Baculoviruses Expressing Foreign Genes for . . . ," in *Pest Control with Enhanced Environmental Safety*, (Duke et al., eds.), ACS Sympos. Series #524, Am. Chem. Soc. (1993), pp. 281–297.

Bonning and Hammock, "Development and Potential of Genetically Engineered Viral Insecticides," *Biotechnol. Genetic Engeinnering Rev.*, 10 (1992), pp. 455–489.

Hammock et al., "Cloning, Expression and Biological Activity of the JHE from *Heliothis virescens*," in *Molecular Insect Science* (Hagedorn et al., eds.), Plenum Press (1990), pp. 49–56.

Bonning et al., "Superior Expression of JHE and β–Galactosidase from the Basic Protein Promoter of *Autographa californica* Nuclear Polyhedrosis Virus Compared to the . . . ," *J. Gen. Virol.*, 75 (1994), pp. 1551–1556.

Harshman et al., "Cloning, Characterization and Genetics of the JHE Gene from *Heliothis virescens*," *Insect. Biochem. Molec. Biol.*, 24:7 (1994), pp. 671–676.

Ichinose et al., "Pharmacokinetics and Tissue Uptake of the Recombinant JHE in Insects" in *Pesticides/Environment: . . .* (Mitsui et al., eds.), Proc. of 1st Int'l. Symp. on Pest. Sci., Pesticide Sci. Soc. of JP (1993).

Bonning et al., "Insect Control by Use of Recombinant Baculoviruses Expressing JHE," in *Natural and Engineered Pest Management Agents* (Hedin et al., eds.), ACS Symp. Ser. #551, Am. Chem. Soc. (1994), pp. 368–383.

Roelvink et al., "Dissimilar Expression of *Autographa californica* Multiple Nucleocapsid Nuclear Polyhedrosis Virus Polyhedrin and p10 Gene," *J. Gen. Virol.*, 73 (1992), pp. 1481–1489.

Booth et al., "Localization of JHE During Development in Normal and in Recombinant Baculovirus–Infected Larvae of the Moth *Trichoplusia ni*", *Tissue & Cell*, 24:2 (1992), pp. 267–282.

Harshman et al., "Effects of Recombinant Juvenile Hormone Esterase on *Aedes aegypti*," *Proc. Calif. Mosq. Vector Control Assoc.*, (1991), pp. 77–80.

Hammock, "Regulation of Juvenile Hormone Titer: Degradation," in *Comprehensive Insect Physiology, Biochemistry, and Pharmacology* (Kerkut and Gilbert, eds.) Pergamon Press (1985), pp. 431–472.

Jones and Hammock, "Prepupal Regulation of Juvenile Hormone Esterase through Direct Induction by Juvenile Hormone," *J. Insect Physiol.*, 29:6, (1983), pp. 471–475.

Sparks and Hammock, "A Comparison of the Induced and Naturally Occurring Juvenile Hormone Esterases from Last Instar Larvae of *Trichoplusia ni*," *Insect Biochem.*, 9, (1979), pp. 411–421.

Sparks et al., "Effects of the Anti Hormone–Hormone Mimic ETB on the Inductio nof Insect Juvenile Hormone Esterase in *Trichoplusia ni*", *Life Sci.*, 25 (1979), pp. 445–450.

Zlotkin et al., "The Effect of Scorpion Venom on Blowfly Larvae—A New Method for the Evaluation of Scorpion Venoms Potency," *Toxicon*, 9 (1971), pp. 1–8.

Zlotkin et al., "An Excitatory and a Depressant Insect Toxin from Scorpion Venom both Affect Sodium Conductance and Possess a Common Binding Site," *Arch. Biochem. & Biophys.*, 240:2 (Aug. 1985), pp. 877–887.

Adachi et al., "cDNA Structure and Expressio nof Bombyxin, and Insulin–like Brain Secretory Peptide of the Silkworm *Bombyx mori*," *J. Biol. Chem.*, 264:13 (1984), pp. 349–358.

Maeda, "Increased Insecticidal Effect by a Recombinant Baculovirus Carrying a Synthetic Diuretic Hormone Gene," *Biochem. & Biophys. Res. Comm.*, 165:3 (1989), pp. 1177–1183.

Carbonell et al., "Synthesis of a Gene Coding for an Insect–Specific Scorpion Neurotoxin and Attempts to Express it Using Baculovirus Vectors," *Gene*, 73, pp. 409–418 (1988).

Carbonell et al., "Baculovirus Interaction with Nontarget Organisms: a Virus–Borne Reporter Gene is Not Expressed in Two Mammalian Cell Lines," *Appl. Environ. Microbiol*, 53:7 (Jul. 1987), pp. 1412–1417.

Dee et al., "Expression and Secretion of a Functional Scorpion Insecticidal Toxin in Cultured Mouse Cells," *Bio/Technology*, 8, (Apr. 1990), pp. 339–342.

Cameron et al., "Insect Cell Culture Technology in Baculovirus Expression Systems," *Trends in Biotechnology*, vol. 7 (1989), pp. 66–70.

Moffat, Anne Simon, "New Chemicals Seek to Outwit Insect Pests," *Science*, 261, pp. 550–551 (1993).

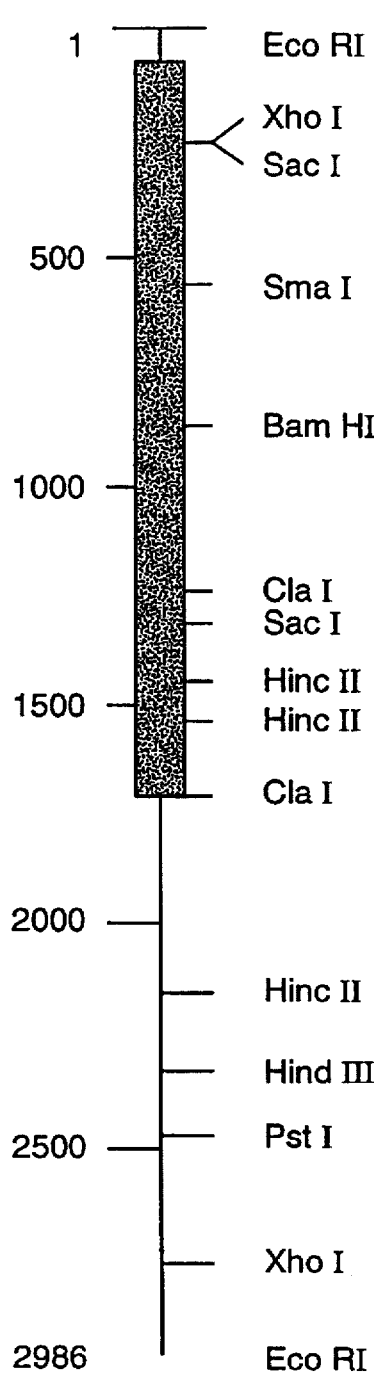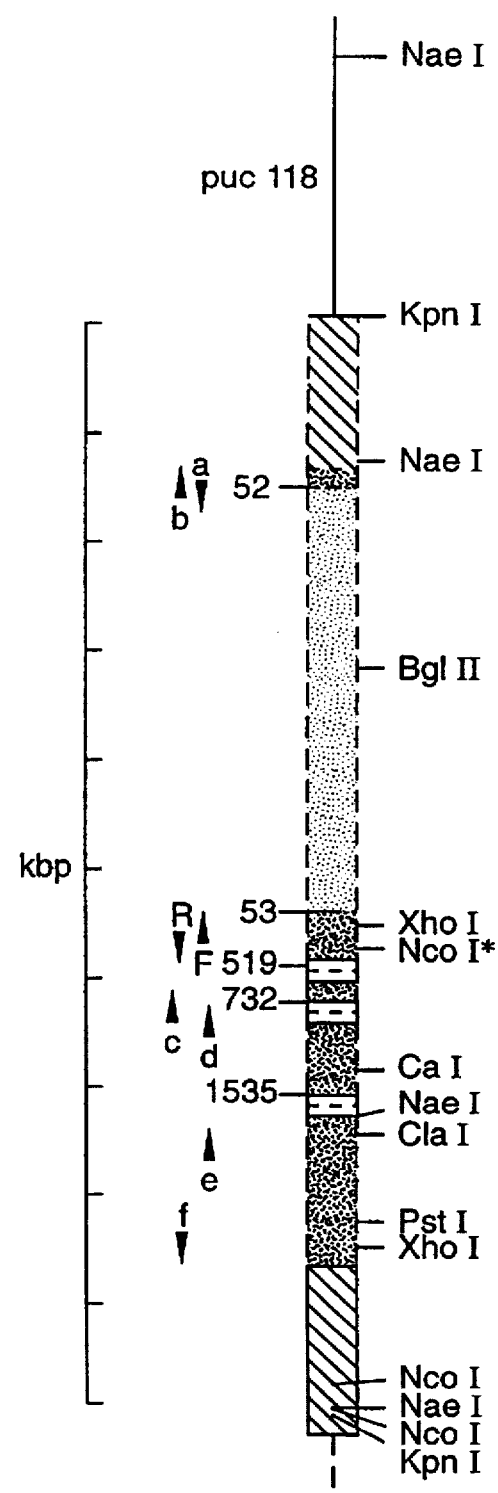
FIG._1
FIG._2

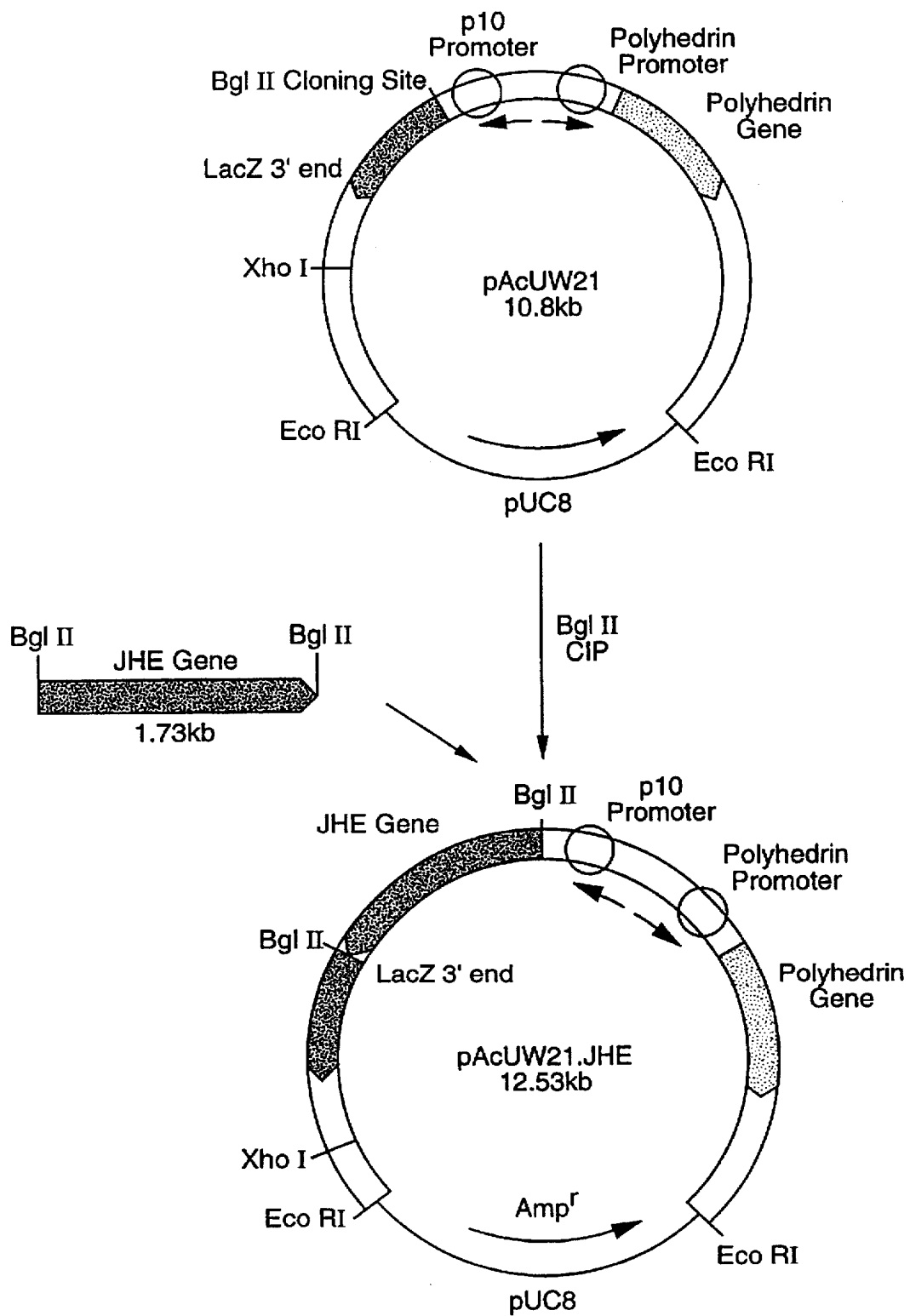
FIG._3

```
M T S H V L A L A F L L H A C T A L A    W   Q   E   T . . . . . .
                                 . . . . . TGG CAG GAG ACA . . . . .
           C TCC ATG GAA TTC ATG TGG CAG GAG ACA
             Nco I   Eco RI   M   W   Q   E   T
```
FIG._4A
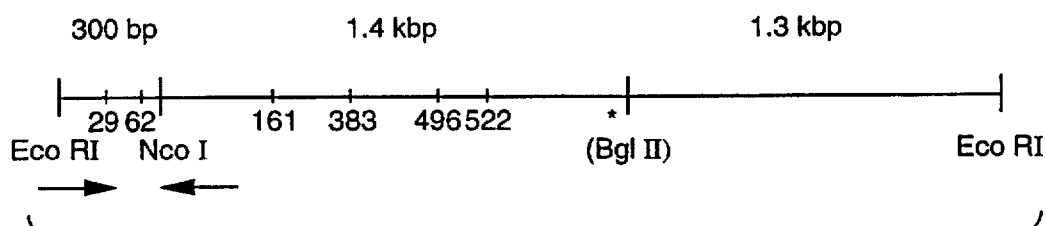
FIG._4B

INSECT DIAGNOSTIC AND CONTROL COMPOSITIONS WITH TRUNCATED JHE

This is a continuation-in-part of application Ser. No. 07/927,851, filed Aug. 10, 1992, which is a continuation in part of U.S. Ser. No. 07/725,226, filed Jun. 26, 1991, now abandoned, which was a continuation of Ser. No. 07/265,507, filed Nov. 1, 1988, now abandoned.

This invention was made with Government support under NIH Grant No. DCB 91-19332, awarded by the National Science Foundation and Grant No. 91-37302-6185, awarded by the United States Department of Agriculture (USDA). The government has certain rights in this invention.

FIELD OF THE INVENTION

The present invention relates to uses of nucleotide sequences coding for juvenile hormone esterase mutants, and more particularly to recombinant expression vectors including a modified coding sequence of juvenile hormone esterase for uses such as in controlling insects.

BACKGROUND OF THE INVENTION

The lepidopteran family Noctuidae includes some of the most destructive agricultural pests, such as the genera Heliothis, Helicoverpa, Spodoptera and Trichoplusia. For example, included in this family are the tobacco budworm (*Hellothis virescens*), the cotton leafworm (*Alabama argillacea*), the spotted cutworm (*Amathes c-nigrum*), the glassy cutworm (*Crymodes devastator*), the bronzed cutworm (*Nephelodes emmedonia*), the fall armyworm (*Laphygma frugiperda*), the beet armyworm (*Spodoptera exigua*) and the variegated cutworm (*Peridroma saucia*). Juvenile hormone esterase is responsible for the stage-specific metabolism of juvenile hormone in such insects.

Juvenile hormone and juvenile hormone esterase have been studied extensively in the Lepidoptera. In the final larval growing stage of these insects, there is a rapid decline in the juvenile hormone titer which initiates the physiological and behavioral events preceding pupation and adult development. Juvenile hormone esterase has been suggested for insect control by administering the esterase during a larval stadium to disrupt normal development. U.S. Pat. No. 5,098,706, issued Mar. 24, 1992, inventors Hammock et al.

In copending Ser. No. 07/927,851, expression vectors are described in recombinant expression vector that halts feeding and disrupts the development of pests in the noctuid family by artificial expression of juvenile hormone esterases at an early stage of development. The recombinant expression vector may be a baculovirus. Such a recombinant strategy to control insect pest populations holds promise, particularly since the wide-scale resistance of pests to organic insecticides, such as pyrethroids, has begun to result in substantial crop losses. In cotton alone, the presence of Pyr-R Heliothis species has resulted in millions of lost dollars annually. In fact, in several cases pyrethroid insecticides have completely failed to control infestations of Heliothis larvae in cotton, which has resulted in complete destruction of the crop.

Other recombinant strategies include the modification of the nuclear polyhedrosis virus *Autographa californica* (AcNPV), from the family Baculoviridae, for an increased speed of kill by expressing insect-selective toxins. The introduction of an insect-selective toxin into an insect-pathogenic virus has resulted in a reduction in the killing time of insect hosts, as is described by U.S. Ser. No. 08/229,417, filed Apr. 15, 1994, which is a continuation-in-part application of U.S. Ser. No. 07/629,603, filed Dec. 19, 1990, having (in part) common assignment herewith. In another copending application, of common assignment herewith, U.S. Ser. No. 08/279,956, filed Jul. 5, 1994, insect control is described with a synergistic combination of recombinant virus and an organic insecticide.

Nevertheless, there is a continued need for compositions and methods which will lead to rapid insect death, disruption of development, and/or cessation of feeding to assist in controlling insect pest populations.

SUMMARY OF THE INVENTION

It is one object of the present invention to provide a recombinant expression vector that halts feeding and disrupts the development of insect pests at an early stage of development.

A preferred use of the inventive recombinant vector is for expression in insects by infecting susceptible host insect cells with a recombinant baculovirus so that insect development is disrupted.

Thus, in one aspect of the present invention, a recombinant expression vector capable of expression in a host insect includes a coding sequence for a truncated protein of a juvenile hormone esterase. For example, a recombinant baculovirus embodiment derived from the nucleopolyhedrosis virus of *Autographa californica* has been constructed. This recombinant embodiment expresses a modified (truncated) form of juvenile hormone esterase (JHE) in that a plurality of N-terminal amino acid residues are missing. As a consequence, the protein does not become glycosylated and does not leave the cell in which expression has occurred.

A preferred embodiment is a recombinant *Autographa californica* nuclear polyhedrosis virus in which a modified JHE gene has been cloned. The modified JHE gene does not express the signal sequence which targets the enzyme to the plasma membrane and thus the resulting protein is cytoplasmic and nonglycosylated.

These and other aspects and advantages of the present invention will now be more fully described.

BRIEF DESCRIPTION OF THE DRAWINGS

FIG. 1 illustrates a restriction map for a cDNA coding for juvenile hormone esterase (3hv21);

FIG. 2 summarizes the JHE gene itself;

FIG. 3 graphically illustrates construction of a plasmid embodiment; and,

FIG. 4A is a detail of the 5' end of JHE while FIG. 4B a map of JHE with the locations of two PCR primers shown by arrows.

DETAILED DESCRIPTION OF THE PREFERRED EMBODIMENTS

The lepidopteran family Noctuidae includes a number of economically destructive agricultural pests. Briefly, two epithelial hormones control metamorphosis in such insects. Asteroid hormone, 20-hydroxyecdysone, causes the molt, while a terpenoid hormone, juvenile hormone (JH), determines the nature of the molt. If juvenile hormone titers are high, then the molt is isometric to a larger larval stage. If juvenile hormone titers are low, then an anisometric molt to a pupal stage will occur. Thus, the initial reduction in juvenile hormone titer in the last larval stadium is a key event in insect development in that it initiates a sequence of events leading to pupation and early in this sequence of events is the cessation of feeding. This reduction in juvenile hormone titer is accomplished by a reduction of biosynthesis and a tremendous increase in the highly aggressive enzyme known as juvenile hormone esterase (JHE).

Juvenile hormone esterase is an insect protein which appears at critical times in the insect's life. It appears to present no risk to other groups of organisms. It is nonlethal to an individual cell which allows and perhaps encourages viral replication; yet the enzyme will fatally disrupt the normal development of the organism. Because the substrate (juvenile hormone) readily penetrates membranes, the juvenile hormone esterase need only be expressed in a few cells to deplete juvenile hormone. Differential tissue depletion of juvenile hormone is likely to be even more rapidly fatal to an insect than uniform depletion.

Numerous attempts had previously been made to purify juvenile hormone esterases, but purification of the low abundance enzyme from a small tissue source had proven very tedious. U.S. Pat. No. 5,098,706, issued Mar. 24, 1992, and filed concurrently with Ser. No. 07/265,507 of which this is in a chain of continuation-in-part applications, exemplifies the administration of an affinity purified enzyme to insects which results in anti-juvenile hormone activity. Such anti-juvenile hormone activity is effectively lethal, for example in blocking damage by herbivorous insects.

When baculovirus-expressed full length JHE is produced in an insect, it is secreted from the affected cells into the insect circulatory system because the N-terminal amino acids of the protein are a signal for the newly made protein to enter the secretory pathway and become glycosylated. In the glycosylated form, the JHE exists the cell and enters the insect's circulatory system. Once there, it is rapidly taken up and degraded by insect pericardial cells. The end result of the removal of JHE from the circulatory system, is that a baculovirus expressing full length JHE has reduced insecticidal activity.

We have improved the insecticidal activity of JHE by truncating the DNA coding sequence for the N-terminal 19 amino acids of the protein. As a consequence, the protein does not become glycosylated, and does not leave the cell. Thus, by creating a truncated protein that builds up in virus-infected cells within the insect, a dramatic increase in insecticidal activity has been achieved. Recombinant baculovirus expressing the truncated JHE reduces the time taken for the virus to kill the host.

Thus, one aspect of the present invention concerns manipulation of the coding sequence for juvenile hormone esterase. SEQ ID NO:1 sets out the coding sequence for one cDNA of JHE and SEQ ID NO:2 is another cDNA of JHE. These coding sequences are for juvenile hormone esterase from *Heliothis virescens*, although there is homology to *Helicoverpa zea* (formerly *Heliothis zea*), to *Tricoplusia ni* and (at lower stringency) hybridization to *Manduca sexta*. Further, JHE isolated (or derived) from *Heliothis (Helicoverpa) virescens* functions to hydrolyze every known form of JH. This means that a coding sequence for JHE derived from *H. virescens* can be used to isolate the gene or the message from a variety of species. FIG. 2 illustrates the JHE gene for *H. virescens* and gives, among other things, restriction enzyme sites.

We selected the site for mutagenesis as the N-terminal signal for glycosylation. For many site-directed changes it is possible to add, as well as remove, regions of the enzyme that confer defined functions. Other site-directed changes can include alteration of sites resulting in lability to proteases (intra- or extracellular), lysosome recognition sites, tissue (i.e., gut or pericardial) recognition sites, or additional sites involved with ubiquitination. Sites that affect subcellular targeting can also be modified. Endogenous modification of the enzyme, for example acylation or phosphorylation, can be a goal of mutagenesis. Larger-scale modifications of the enzyme are also possible. For instance, C-terminal truncated forms of JHE have already been shown to retain catalytic activity.

Generation of chimeric proteins is another possibility. One could make chimeric proteins with added peptides to provide dual catalytic activity, increase production in an expression system, and/or change pharmacokinetic properties in a target organism. Thus it may be useful to make a JHE/β-galactosidase enzyme or a JHE/acetyl cholinesterase enzyme. Since X-ray analysis of esterases indicates that they exist in a C-terminal and N-terminal domain it is straightforward to make chimera of various esterases to alter substrate specificity, kinetic properties, or pharmacokinetic properties.

The CDNA or gene may be altered to change mRNA dynamics, rate of transcription, or rate of translation.

JHE Coding Sequence Cloning

As will also be described in Examples 1 and 2, the clone containing the sequence of the mRNA transcript of juvenile hormone esterase from *Heliothis virescens* may be isolated from a lambda gt-11 expression library. To make the expression library, total RNA was isolated by homogenizing fat bodies in guanidinium thiocyanate and centrifugation through cesium chloride. The fat bodies were from last instar larvae that had been treated with epofenonane 24 hours previously. Poly-adenylated RNA was prepared by one cycle of oligo-dT chromatography from which cDNA was synthesized and size selected for greater than 1350 base pairs. The size selected cDNA was suitably processed and ligated to arms of a lambda-gt11 phage expression vector. The ligated DNA was then packaged into phage heads, infected into host cells and plated on a lawn of host *E. coli*. The cDNA library was not amplified prior to screening.

Screening was done immunochemically on nitro-cellulose filters to which proteins from plated phage had been bound after induction of protein synthesis. Clones reacting with antibodies specific for juvenile hormone esterase were plaque-purified after detection with immunohistochemical means. A second round of screening was then conducted upon the isolated clones with hybridization to a mixture of synthetic nucleotides complementary to the deduced mRNA sequence possibilities determined from the N-terminal amino-acid sequence of juvenile hormone esterase.

The amino acid sequence was determined by automated Edman degradation of the purified protein. From this round of screening, three 3,000 basepair clones, 3hv1, 3hv16 and 3hv21 were isolated, subcloned into plasmids and subjected to restriction analysis. The clone 3hv21 has its sequence given by SEQ ID NO. 1 while that of 3hv16 is SEQ ID NO:2. The length of clone 3hv21 matched the 3,000 basepair length of the juvenile hormone esterase mRNA transcript as determined by Northern blotting with radiolabeled DNA of clone 3hv21. An 840 basepair fragment of the 5' coding region of 3hv21 was then sequenced. The sequence confirmed the clone to be that coding for juvenile hormone esterase as the deduced amino-acid sequence matched 33 of the 35 of the doubly confirmed amino-acids sequenced at the N-terminus of the purified protein.

Uses of Modified JHE Coding Sequences in Microbes

The present invention relates to the use of genetically engineered, insecticidal microbes to treat pests such as insects. Expression of the modified JHE coding sequence gene is accomplished by infecting susceptible host insect or plant cells with recombinant microbes.

Although recombinant baculoviruses will be used throughout as an illustration of preferred microbes, this invention can be practiced with a variety of microbes as recombinant delivery systems. Thus, the JHE coding sequence can be mutated or modified and inserted into a vector such as a baculovirus, a fungi, a DNA or RNA virus, or bacteria.

On the order of forty nuclear polyhedrosis viruses have been isolated from insect species. (See, for example, *Atlas of Invertebrate Viruses*, Adams and Bonami, editors, CRC Press, Inc., 1991.) Various baculoviruses, including those that infect cotton bollworm, *Helicoverpa zea*, tobacco budworm, *Heliothis virescens*, Douglas fir tussock moth, *Orgia pseudotsugata*, gypsy moth, *Lymantria dispar*, alfalfa looper, *Autographa californica*, European pine fly, *Neodiprion sertifer*, and codling moth, *Laspeyresia pomonella*, have been registered as pesticides and all such baculoviruses from insect species are suitable for practicing the invention.

Numerous fungi are capable of infecting insects. Introduction of the insect-selective toxin into the genome of such fungi could enhance the potency as pesticides. For example, *Beauvaria bassania* and *Beauvaria brongniartii* have a wide host range and have been suggested as candidates for microbial pesticides (see review by Miller et al., *Science*, 219:715–721, 1983).

Bacteria (other than *Bacillus thuringiensis*) that have been considered as insect control agents include *Bacillus popilliae*, *B. lentimorbus*, and *B. sphaericus*. Their potential as pesticides can be enhanced by improving their potency through the incorporation of an insect-selective toxin into their genome.

As earlier mentioned, preferred insecticidal microbes for practicing the invention are baculoviruses. By "baculovirus" is meant any baculovirus of the family Baculoviridae, such as a nuclear polyhedrosis virus (NPV). Baculoviruses are a large group of evolutionarily related viruses, which infect only arthropods; indeed, some baculoviruses only infect insects that are pests of commercially important agricultural and forestry crops, while others are known that specifically infect other insect pests. Because baculoviruses infect only arthropods, they pose little or no risk to humans, plants, or the environment.

Of the suitable DNA viruses, in addition to the Baculoviridae are the entomopox viruses (EPV), such as *Melolontha melonotha* EPV, *Amsacta moorei* EPV, *Locusta migratoria* EPV, *Melanoplus sanguinipes* EPV, *Schistocerca gregaria* EPV, *Aedes aogypti* EPV, and *Chironomus luridus* EPV. Other suitable DNA viruses are granulosis viruses (GV). Suitable RNA viruses include togaviruses, flaviviruses, picornaviruses, cytoplasmic polyhedrosis viruses (CPV), and the like. The subfamily of double stranded DNA viruses Eubaculovirinae includes two genera, NPVS and GVs, which are particularly useful for biological control because they produce occlusion bodies in their life cycle. Examples of GVs include *Cydia pomonella* GV (coddling moth GV), *Pieris brassicae* GV, *Trichoplusia ni* GV, *Artogeia rapae* GV, and *Plodia interpunctella* GV (Indian meal moth).

Suitable baculoviruses for practicing this invention may be occluded or non-occluded. The nuclear polyhedrosis viruses ("NPV") are one baculovirus subgroup, which are "occluded." That is, a characteristic feature of the NPV group is that many virions are embedded in a crystalline protein matrix referred to as an "occlusion body." Examples of NPVs include *Lymantria dispar* NPV (gypsy moth NPV), *Autographa californica* MNPV, *Anagrapha falcifera* NPV (celery looper NPV), *Spodoptera litturalis* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV, and *Rachiplusia ou* NPV. For field use occluded viruses often are preferable due to their greater stability since the viral polyhedrin coat provides protection for the enclosed infectious nucleocapsids.

Among illustrative, useful baculoviruses in practicing this invention are those *Anagrapha falcifera*, *Anticarsia gemmatalis*, *Buzura suppressuria*, *Cydia pomonella*, *Helicoverpa zea*, *Heliothis armigera*, *Manestia brassicae*, *Plutella xylostella*, *Spodoptera exigua*, *Spodoptera littoralis*, and *Spodoptera litura*. A particularly useful "NPV" baculovirus for practicing this invention is AcNPV, which is a nuclear polyhedrosis virus from *Autographa californica*. *Autographa californica* is of particular interest because various major pest species within the genera Spodoptera, Trichoplusia, and Heliothis are susceptible to this virus.

An early report describing preparation of recombinant baculoviruses was given in U.S. Pat. No. 4,745,051, issued May 17, 1988, inventors, Smith, et al., incorporated herein by reference, which describes a method for producing a recombinant baculovirus expression vector capable of expression of a selected gene in a host insect cell. The method exemplified by U.S. Pat. No. 4,745,051 was used to express β-Interferon by infecting susceptible host insect cells with a recombinant baculovirus expression vector. Briefly, baculovirus DNA is cleaved to obtain a DNA fragment containing at least a promoter of the baculovirus gene. One baculovirus gene is that coding for polyhedrin, since the polyhedrin protein is one of the most highly expressed eucaryotic genes known, although other promoter and hybrid promoter sequences may be used. Here, the gene cloned into the baculovirus expresses a modified JHE rather than β-Interferon.

The preferred baculovirus utilized is *Autographa californica*, although other baculovirus strains may be suitably utilized. *Autographa californica* (AcNPV) is of particular interest as various major pest species within the genera Spodoptera, Trichoplusia, and Heliothis are susceptible to this virus.

In the present invention, a baculovirus may be modified such as described by the method described by U.S. Pat. No. 4,745,051, but by utilizing a mutant of the JHE coding sequence rather than the β-Interferon gene. A recombinant expression vector thus comprises a mutated JHE under the control of a promoter sequence (such as the polyhedrin, p10 or basic protein promoters), which is heterologous with the mutated JHE coding sequence and which regulates the transcription thereof.

Aspects of the present invention will be illustrated by a number of examples. Examples 1 and 2 primarily describe work obtaining cDNA for JHE and some characterizations for the JHE gene. Example 3 describes the construction of a recombinant baculovirus embodiment of the invention. Examples 4 and 5 discuss other aspects and embodiments of the invention, as does Example 6. Examples 7 and 8 describes biological activity of the inventive recombinants in comparison to other recombinants.

EXAMPLE 1

Animals

Larvae of *Heliothis virescens* were obtained from a research facility of Dow Chemical Company located at Walnut Creek, Calif.

Materials

Radioactively labeled reagents obtained from Amersham (Arlington Heights, Ill.). Other chemicals were of the highest quality available. Enzymes were obtained from Promega Biotec (Madison, Wis.), Boehringer Mannheim Biochemicals, (Indianapolis, Ind.), United States Biochemical Corporation (Cleveland, Ohio) and Sigma (St. Louis, Mo.).

A Bluescript plasmid with a cDNA insert from *H. virescens*, 3hv1 (sequence not shown), 3hv21 (SEQ ID NO:1), and 3hv16 (SEQ ID NO:2), was isolated from the *E. coli* host cells and host chromosomal DNA using the alkaline lysis miniprep procedure described in Maniatis et al., *Molecular Cloning*, Cold Spring Harbor Laboratory (1982). The N-terminal Bam HI restriction fragment from the above preparation was ligated into phage M13 (mp19). Thus, in a 25 μl volume 0.2 μg of Bam HI cut mp19 was added to 1.0 μg of Bluescript plasmid cut with Bam HI. After the addition of ligase the reaction was allowed to proceed 60 minutes at room temperature and overnight at 4° C.

Ligated DNA was used to transform competent *E. coli* host cells are described in Rodriguez, *Recombinant DNA Techniques: An Introduction*, Addison-Wesley (1983). Either 0.1 μl, 1 μl or 10 μl of the ligation mixture was added to 200 μl of competent JM101. After incubation on ice the mixture was added to soft agarose at 43°–45° C. for 2 minutes. The agarose and cells were plated with X-gal and IPTG, and incubated at 37° C.

Recombinant transformants were present as white plaques.

Isolated white plaques were picked and grown for 6 hours at 37° C. in 1×YT medium. Double-stranded DNA was prepared by the method described in Rodriquez, supra. Briefly, the host cells were pelleted and resuspended in a sucrose EDTA buffer. RNAse was added and the cells lysed in 1% SDS with 0.2N NaOH. The host chromosome DNA was pelleted by centrifugation and the supernatant with double-stranded RF M13 DNA removed. From the supernatant double-stranded M13 was precipitated in isopropanol and washed with ethanol. The double-stranded M13 was cut with Bam HI and run on a 0.8% agarose gel with Bam HI cut Bluescript plasmid to ensure the subcloned M13 fragment was the same size as the fragment from the original Bluescript plasmid.

The next step was to conduct a C-test for complementary single-stranded DNA from M13 plaques. Identification of both orientations of a cloned insert is useful for single-strand sequencing because it is possible to sequence from both ends toward the middle. Essentially, the transformed host cells (JM101) from independent plaques were grown for 4–6 hours in 1×YT medium. Approximately 8 μl of supernatant from each plaque was removed and supernatant from various combinations of different plaques was mixed with glycerol, salt, and SDS. The mixtures were incubated at 60°–70° C. for 15 minutes and allowed to cool. A sample of the mixture was placed on a 0.8% agarose gel to detect hybridization by retarded migration in the gel.

Single-stranded DNA from M13 with inserts in opposite orientation was then prepared. To do so, transformed cells were grown for 4–6 hours at 37° C. Single-stranded DNA was extruded into the medium and precipitated with PEG and NaCl. After resuspension protein was removed with phenol chloroform. Several volumes of ethanol was added to the aqueous for precipitation. The pellet was washed in 70% ethanol, dried and resuspended in autoclaved water.

Sequencing of the above single-stranded DNA was based on the chain termination method of Sanger et. al, *PNAS*, 74, 5463 (1977). Bam HI fragments in both orientations in M13 were sequenced. For sequencing reactions, $^{32}$P ATP was used with the reagents and instructions supplied in the sequence kit (United States Biochemical). The sequencing reactions were run on 4% and 6% acrylamide gels. Audioradiographs of the gels were read after overnight exposure of the film to dried gel. The complete Bam HI insert of approximately 840 base pairs was read. This included the putative sequence for the secretion signal peptide and the N-terminal coding sequence which corresponded to the N-terminal amino acid sequence for JHE. The identity of the JHE cDNA insert was initially established in this manner.

EXAMPLE 2

Protein Sequencing

Juvenile hormone esterase was purified (as described by Abdel-Aal and Hammock, *Science*, 233, pp. 1073–1076 (1986)) from the hemolymph of last instar larvae of *Heliothis virescens*. The purified preparation was seen to be a single band when analyzed by electrophoresis in the presence of SDS (Laemmli, *Nature*, 227, pp. 680–685 (1970)) and isoelectric focusing on a polyacrylamide gel having a ph 4.0 to pH 6.5 gradient (Pharmacia, Piscataway, N.J.). However, when subjected to Edman degradation, two proteins were indicated to be in the preparation. The presence of isoforms of JH esterase in *H. virescens* is consistent with observations of the enzyme in other insects. From the major form was obtained a readable sequence of 35 residues. The signal from the minor form indicated a protein having a two residue extension of Ser-Ala followed by a sequence of five residues identical to the ultimate five residues at the N-terminus of the major form. Amino acid sequencing at the N-terminal of juvenile hormone esterase was done with a Beckman 890M liquid phase sequencer.

Probe Preparation

Both antibodies against juvenile hormone esterase and nucleotides complementary to the juvenile hormone esterase message were used as probes to detect recombinant clones coding for juvenile hormone esterase. Antisera to juvenile hormone esterase was prepared with New Zealand White female rabbits (Vaitukaitis, *Methods in Enzymology* (Langone and Yon Vunakis, eds.) 73, pp. 46–52, Academic Press, New York (1981)). To reduce background, the antisera was incubated overnight at 4° C. with diluted *Heliothis virescens* hemolymph devoid of juvenile hormone esterase activity (the antisera was diluted 1:10 in a solution of 10 mg/ml hemolymph protein in pH 7.4, I=0.2 phosphate buffer containing 0.01% phenyl thiourea). A final dilution of 1:750 was used for screening. A mixture of 32 14-mer nucleotides were synthesized using a Syntec model 1450 synthesizer. Their sequences were complementary to all the possibilities of the mRNA structure deduced from the amino acid sequence of the N-terminal. The nucleotides were purified on a Nensorb 20 nucleic acid purification cartridge (Dupont Co., Wilmington, Del.) and end-labeled with $^{32}$P with T4 polynucleotide kinase and [$^{32}$P]ATP (>6000 Ci/mmol) by a standard technique (Zeff and Geliebter, *BRL Focus* 9-2, pp. 1–2 (1987)).

CDNA Synthesis and Cloning

Total RNA was isolated by homogenizing fat bodies in guanidinium thiocyanate and centrifugation through cesium chloride (Turpen and Griffith, *BioTechniques* 4(1), pp. 11–15 (1986)). The fat bodies were dissected from last instar larvae that had been treated with epofenonane 24 hours previously to increase the level of juvenile hormone esterase activity (Hanzlik and Hammock, *J. Biol. Chem.*, 262, pp. 13584–13591 (1987)). At the time of treatment, the larvae weighed 200–300 mg. Polyadenylated RNA was prepared by one cycle of oligo-dT chromatography (Aviv and Leder, *Proc. Nat. Acad. Sci. USA*, 69, pp. 1408–1412 (1972)) using oligo-dT cellulose (Collaborative Research, Cambridge, Mass.). Synthesis of cDNA from 2 μg of poly-A RNA was done by the method of Gubler and Hoffman (Gubler and Hoffman, *Gene*, 25, pp. 263–269 (1983)) with a cDNA kit (Amersham) and a variation of its protocol. The protocol was varied in the priming of the first strand synthesis wherein 100 ng of random hexamer primers (Pharmacia) were added 30 minutes after initiation of first strand synthesis by oligo-dT primers done according to the protocol. Size selection of the cDNA for >1350 basepairs was done with gel permeation using a spin column (5 Prime-3 Prime, Paoli, Pa.). The size selected cDNA was treated with Eco R1 methylase, ligated to Eco R1 linkers and treated with Eco R1 restriction endonuclease according to the protocols presented by Huynh et al. (Huynh, Young and Davis, *DNA Cloning: A Practical Approach* (Glover, D. M., ed.), pp. 49–78, IRL Press, Oxford (1984)). The free linkers were removed by three cycles of ultrafiltration using Centricon 30 microfiltrators (Amicon, Danvers, Mass.). The cDNA was then ligated to arms of a lambda gt11 expression vector derivative (lambda-ZAP, Stratagene Cloning Systems, La Jolla, Calif.) according to the manufacturer's recommendations. The ligated DNA was then packaged into phage heads using a two extract system (Gigapack Gold, Stratagene Cloning Systems), and plated on to rec *E. coli* host cells (XL1-Blue, Stratagene Cloning Systems). Greater than 99% of the clones were recombinant. The cDNA library was not amplified prior to screening.

Screening

Initial screening was done immunochemically on nitrocellulose filters to which proteins from plated phage had been bound after induction of protein synthesis. Clones reacting with antibodies specific for juvenile hormone esterase were plaque-purified after detection with immunohistochemical means (9) using a kit (Protoblot, Promega). A second round of screening was then conducted upon plaque lifts of the isolated clones by hybridization to the mixture of 14-mer nucleotides. This was done by incubating the filters with the labeled oligomers at 35° C. in 5× SSPE, 3× Denhardt's solution, 100 µg/ml low molecular weight DNA after prehybridizing in the same solution sans the oligomers. Washing was done three times at the hybridizing temperature in a solution consisting of 2× SSC and 0.1% SDS. Positively reacting clones were then subcloned into the Bluescript SK M13-plasmid (Stratagene Cloning Systems) by the automatic excision process allowed by the lambda-ZAP vector.

Sequencing

Sequencing of the remaining cDNA insert, and to confirm the 840 base pair sequence, was done with the dideoxy chain termination method (Sanger, Nicklen and Coulson, *Proc. Natl. Acad. Sci. USA*, 74, pp. 5463–5467 (1977)) using modified T7 DNA polymerase (Sequenase, United States Biochemical Corp.) and 35S labeled dATP. Templates were generated by using both denatured plasmids (Toneguzzo, Glynn, Levi, Mjolsness, and Hayday, *BioTechniques*, 6, pp. 460–469 (1988)) and single stranded DNA from M13 phage (Yanisch-Perron, Vieira, and Messing, *Gene*, 33, pp. 103–119). A rec A- *E. coli* strain (JM109) was used for the amplification of the subclones that were constructed with both restriction fragments and nested deletions (Henikoff, *Gene*, 28, pp. 351–359 (1984)) (kit from Stratagene Cloning Systems). Computer assisted sequence analysis was done with programs written by Pustell (Pustell and Kafatos, *Nucleic Acids Res.*, 12, (1984)).

Additional Library and Sequence Analysis

Another cDNA expression library was constructed using both random and oligo-dT priming of the first strand. In addition we used cDNA selected for a size greater than 1350 bp for ligation to the vector. Screening 40,000 clones of this library produced 25 immunoreactive clones, five of which hybridized to the nucleotide probes. Three of these clones, designated 3hv1, 3hv16 and 3hv21, were subcloned into plasmids and characterized. All three clones contained 3000 bp inserts that had identical restriction patterns when incubated with Eco RI, Xho I and Bam HI. When the clone, 3hv21, was used as a probe on a Northern blot, it hybridized at low stringency to a single band with a 3.0 kb length.

The amount of screening required to isolate positive clones indicates that the frequency of the JH esterase message during the period of its secretion into the hemolymph during the last instar is relatively low.

The three clones (3hv1, 3hv21, and 3hv16) were considered to be identical due to their identical length and restriction patterns, although slight differences exist as discussed hereinafter. The sequence of clone 3hv21 is shown by SEQ ID NO:1 (was set out by FIG. 2 of Ser. Nos. 07/725,226 and 07/265,507 of which this is in a chain of continuation-in-parts and published in the *Journal of Biological Chemistry*, 264:21, pp. 12419–12425 (1989). FIG. 1 shows a restriction map for this clone. The clone was sequenced 100% in both directions. (The other clone 3hv16 was used for baculovirus expression, mutagenesis, and bioassays.)

SEQ ID NO:1 shows the cDNA sequence of JH esterase, which is a 2989 bp cDNA clone and is nearly a full length copy of the mRNA transcript. There is a short 19 base sequence prior (5') to the first ATG. The position and composition of the bases immediately prior to the first ATG matches the consensus for an insect ribosome binding site except at position −3 where a G (the second most frequent base at this site) replaces an A. After the first ATG, there is a 1714 bp open reading frame followed by an untranslated 1256 bp region including a 12 base poly(A) tail. Translation of the open reading frame predicts a 563 residue protein. The sequence and composition of the 19 residues prior to the N-terminal Trp of the secreted major form of JH esterase match well with the consensus for signal peptides for secretion. The molecular weight of the mature protein (sans signal peptide) is predicted to be 61,012 Da, which is in agreement with the $M_r$ of 62,000 derived from electrophoresis. The sequences of the ultimate 35 amino acids derived from Edman degradation of the major form of JH esterase and that predicted by the cDNA sequence match except at two sites. The residues Val 10 and Phe 33 predicted by the sequence of clone 3hv21 are indicted to be Leu and Pro, respectively, on the sequenced protein (Table A).

TABLE A

| Amino acid sequence analysis of the N-terminus of JB esterase from *H. virescens*[1] | | |
|---|---|---|
| Cycle | Residue(s)[2] | Yield[3] |
| 1 | Trp (Ser) | 1120 (230) |
| 2 | Gln (Ala) | 780 (360) |
| 3 | Glu (Trp) | 870 (340) |
| 4 | Thr (Gln) | 100 (310) |
| 5 | Asn (Glu) | 800 (350) |
| 6 | Ser (Thr) | 560 (10) |
| 7 | Arg (Asn) | 400 (390) |
| 8 | Ser | 610 |
| 9 | Val | 740 |
| 10 | Leu | 550 |
| 11 | Ala | 340 |
| 12 | His | 380 |
| 13 | Leu | 580 |
| 14 | Asp | 590 |
| 15 | Ser | 460 |
| 16 | Gly | 360 |
| 17 | Ile | 290 |
| 18 | Ile | 390 |
| 19 | Arg | 290 |

TABLE A-continued

Amino acid sequence analysis of the N-terminus
of JB esterase from *H. virescens*[1]

| Cycle | Residue(s)[2] | Yield[3] |
|---|---|---|
| 20 | Gly | 360 |
| 21 | Val | 300 |
| 22 | Pro | 110 |
| 23 | arg | — |
| 24 | Ser | 130 |
| 25 | Ala | 250 |
| 26 | Asp | 190 |
| 27 | arg | — |
| 28 | ile | — |
| 29 | Lys | 170 |
| 30 | phe | — |
| 31 | Ala | 130 |
| 32 | ser | — |
| 33 | Pro | 140 |
| 34 | — | — |
| 35 | gly | — |

[1] Affinity purified JH esterase was subjected to automated Edman degradation on a Beckman model 890M liquid phase sequencer. Derivatized residues were confirmed with two HPLC systems employing reverse phase- and cyano- columns. The amount of protein analyzed was 3 nmol as calculated by Coomasie Blue dye binding.
[2] The initial cycles had strong secondary signals, the identity of which are shown in parenthesis. Residues are capitalized where the identity of the PTH-amino acids were confirmed twice by elution from the two different HPLC systems and are lower case where the identify was assigned on the basis of elution from only one HPLC system.
[3] Yield of secondary PTH-amino acids are shown in parenthesis. Hyphens denote where the yield was not calculated for residues identified on the basis of elution from only one HPLC system.

In addition, the serine present at the N-terminal of the minor form of JH esterase protein that was sequenced is indicated to be Leu −2 on the cDNA. To answer the question of whether the differences were due to the cloning process or were genuine, the 5' region of the two other clones, 3hv1 and 3hv16, were sequenced which were isolated from the same unamplified library as 3hv21.

Slight differences among all three clones were found. The sequence of clone 3hv1 translates identically in the N-terminal region as clone 3hv21, but differs at base 94, which is the last position of a code for serine 6. Clone 3hv16 differs at two bases (50 and 104) from clone 3hv21 in the area coding for the N-terminal, one of which causes a substitution of a phenylalanine for leucine 9 and a leucine for valine 10. The substitution of isoleucine for valine at residue position 10 makes the translation of clone 3hv16 match in 34 of 35 amino acid residues determined from the purified protein.

The previous data indicated at least five slightly different translations of genes for JH esterase, which suggests multiple genes or alleles for JH esterase exist in populations of *H. virescens*. Perhaps contributing to the heterogeneity between the cDNA's and protein sequences is the fact that the protein and RNA were extracted from two different colonies of *H. virescens* and represents natural variation.

There are three consensus poly(A) signal sequences (AATAAA) that start at bases 2299, 2315 and 2951. The presence of three signals for polyadenylation may signify alternative processing of the transcript in the 3' region. Strong evidence from studies of another noctuid moth shows that there is a constitutively expressed intracellular form of JH esterase throughout its larval stage and thus the larval stage of *H. virescens*. Thus a means of producing an intracellular as well as a secreted form of JH esterase is indicated to exist.

The protein translated from the cDNA clone contains four asparagine residues, Asn 62, Asn 161, Asn 383 and Ash 496, which are candidates for glycosylation. However, preliminary evidence indicates that should this modification be present on the secreted JH esterase from *H. virescens*, mannose and derivatives of glucose are not present. This information indicates that portions of the JHE sequence can be used to make chimeric esterases of altered properties. Computer analysis of JH esterase sequence Comparison of the translation of clone 3hv21 to protein sequences in the protein data bank of the National Biomedical Research Foundation and to translations of proteins characterized as esterases, lipases and serine hydrolases in GenBank revealed homologies to five proteins. Identical residue matches (gaps were counted as one substitution regardless of length) of 24.2%, 23.8%, 23.2% and 23.2%, respectively, were noted to human pseudocholine esterase, *Drosophila melanogaster* acetylcholine esterase, electric ray acetylcholine esterase, and *Drosophila melanogaster* esterase −6. In addition, homology to a region situated toward the carboxyl terminal of the large thyroid hormone precursor, bovine thyroglobulin was noted.

EXAMPLE 3

All JHE constructs used were made by introducing the JHE cDNA into the transfer vector pAcUW21 under the control of the strong very late promoter p10. This transfer vector contains polyhedrin, so all viruses made with it were occ+. pAcUW21 was cotransfected along with linearized polyhedrin negative AcNPV DNA into *Spodopera frugiperda* cell line IPLB Sf21; recombinant polyhedrin positive viruses were purified to homogeneity by four sequential plaque assays using standard procedures.

A 3 kbp fragment of DNA containing the 1.7 kbp cDNA for JHE, including the 19 amino acid signal sequence, as well as a 1.3 kbp 3'UTR, was obtained from the 3hv16 clone previously described. The JHE was cloned into the Eco R1 site of pAcUW21. The resultant virus is designated AcJHE.

FIG. 4A is a detail of the 5' end of JHE. The top line represents the amino acid sequence of JHE. The amino acids shown in bold are the mature N terminus of the protein. The second line is the DNA sequence that codes for the N terminus of the protein. The third line is the forward primer used for PCR, 2J6PMR4.SEQ. Below the sequence for the primer is shown restriction sites encoded by the primer as well as the amino acids encoded by the primer. The reverse primer, 2J6PMR8.SEQ, is complimentary to the cDNA immediately downstream from the unique Nco 1 site. FIG. 4B is a map of JHE. Relevant restriction sites are shown, as well as the locations of the amino acids changed in the KK and 4N mutants. The stop codon is shown as an asterisk. The locations of the two PCR primers are shown by arrows. To remove the signal sequence, a PCR strategy was employed. The forward primer was 2J6PMR4.SEQ. The reverse primer was 2J6PMRS.SEQ, which is complimentary to the region immediately downstream of the unique Nco 1 site. The template for PCR was JHE wild type. Once amplified, the PCR product, approximately 300 bp long, was gel purified, and cloned into the Srf 1 site of the pCR-Script SK(+) vector (Stratagene, La Jolla, Calif.). dsDNA sequencing of the insert in pCRscript was accomplished using the Sequenase 2.0 Kit (USB, Cleveland, Ohio). The insert contained no errors introduced by the Taq polymerase.

The Nco 1-Eco R1 fragment of 3hv16, comprising the 3' 1.4 kbp of the JHE cDNA, plus the 1.3 kbp 3'UTR region, was ligated to the PCR-derived 5' end of JHE. The ligated DNA, now a complete JHE gene but without the signal sequence, was inserted into the Eco R1 site of pAcUW21 and recombinant virus produced as described above. The resultant virus is designated "AcJHE-minus".

EXAMPLE 4

Site-directed mutagenesis

The cDNA coding sequence for JHE from clone 3hv16B (SEQ ID NO:2) was selected for mutagenesis. This JHE clone is in the plasmid vector pBluescriptSK+ (Stratagene) and prior to commencement of the mutagenesis reactions, the JHE coding region was removed by digestion with the restriction endonuclease BglII and recloned into the same vector to obtain the reverse orientation of the insert in the vector. This allowed rescue of the appropriate sense strand for site-directed mutagenesis and also enabled the removal of the JHE coding region by both EcoRI and BglII restriction endonucleases.

Rescue of the single strand DNA for mutagenesis was carried out by standard techniques using the mutant M13 bacteriophage M13K07. Briefly, the JHE clone was grown in E. coli strain XL1-blue in 1 ml of LB medium containing 50 µg/ml ampicillin. At early log phase, 50 µl of culture was added to 100 µl of M13K07 (3×108 pfu/ml) and incubated at 37° C. for 1 hour then 40 µl was transferred to 20 ml of LBmedia containing 50 µg/ml ampicillin and 50 µg/ml kanamycin. The culture was incubated overnight at 37° C. and ssDNA purified from the culture supernatant as follows. The culture was centrifuged at 2,000 g for 10 minutes then the supernatant was harvested in 800 µl aliquots in 1.5 ml Eppendorf tubes and 200 µl of 2.5M NaCl/20% PEG added to each aliquot. After 15 minutes at room temperature, the samples were centrifuged at 16,000 g for 5 minutes and the supernatant removed. The samples were then recentrifuged for 30 seconds and residual supernatant removed. The pellets were resuspended in 100 µl TE (10 mM Tris HCl pH 8/0.1 mM EDTA) per 4 tubes and each of the 4 aliquots was extracted once with buffer saturated phenol and twice with chloroform then precipitated with ethanol. The purified ssDNA was resuspended in a final volume of 50 µl of TE.

The site-directed mutagenesis reactions were carried out by the method of Kunkel et al. (1985) using mutant nucleotide sequences complementary to the "rescued" coding strand obtained from the pBluescript Phagemid. Sites for mutagenesis were selected as follows. One desired mutation was lysine (29) to arginine because this is a lysine located near the N-terminus of JHE. Another desired mutation was lysine (522) to arginine because this is a lysine located within a potential "PEST" sequence and local enrichment of Pro, Ser, Glu, and Thr. A third desired mutation was serine (201) to glycine because conserved catalytic serine motif of Gly X $Ser_{201}$ X Gly.

However, numerous options exist for modification of the JHE cDNA, or gene, to increase insecticidal activity or modify the catalytic functions of the enzyme. For example, in addition to removal of the signal sequence (and thus preventing glycosylation) it is possible to add, as well as remove, regions of the enzyme that confer defined functions. Other site-directed changes can include alteration of sites resulting in lability to proteases (intra- or extracellular), lysosome recognition sites, tissue (i.e., gut or pericardial) recognition sites, or additional sites involved with ubiquitination. Sites that affect secretion or subcellular targeting can also be modified. Endogenous modification of the enzyme, for example acylation or phosphorylation, can be a goal of mutagenesis. Larger-scale modifications of the enzyme are also possible.

Generation of chimeric proteins is another possibility. One could make chimeric proteins with added peptides to provide dual catalytic activity, increase production in an expression system, and/or change pharmacokinetic properties in a target organism. Thus it may be useful to make a JHE/β-galactosidase enzyme or a JHE/acetyl cholinesterase enzyme. Since X-ray analysis of esterases indicates that they exist in a C-terminal and N-terminal domain it is straightforward to make chimera of various esterases to alter substrate specificity, kinetic properties, or pharmacokinetic properties.

One mutation prepared was designated K29R (lysine 29 mutated to arginine), one as K522R (lysine 522 mutated to arginine), and one as S201G (serine 201 mutated to glycine). All mutations were confirmed by double-stranded sequencing using a sequenase kit (USB). A double mutant of JHE (K29R, K522R, hereinafter referred to as "JHE-KK") was constructed by removal of the N-terminal half of JHE (containing lysine 29) from the pAcUW21.JHE-K522R construct and replacing this with the N-terminal half of JHE from the pAcUW21.JHE-K29R construct. This was done by digesting pAcUW21.JHE-K522R with BamHI which cuts the clone at position 851 in JHE and also cuts the pAcUW21 vector within the polyhedrin gene. This region was then replaced with the equivalent region from pAcUW21.JHE-K29R to regenerate the same vector and clone but containing the K29R mutation. The correct orientation of the modified JHE sequence was confirmed in each case by restriction analysis. Transformation, plasmid preparation and digestions were carried out using standard techniques (Maniatis et al., 1990).

EXAMPLE 5

JHE-KK contains two mutations; the lysines at positions 29 and 522 were changed to arginines by site directed mutagenesis as described in Example 4. In addition to the two lysines, JHE-KK differs from the JHE wild type used here in one other respect. It does not contain a 3'UTR. A Bgl II site was introduced downstream of the stop codon so that most of the 3'UTR could be removed from the final construct. pAcUW21 provides an SV40-derived poly-A signal downstream of the unique cloning sites used for cloning behind the p10 promoter.

To produce a JHE-KK that lacks the signal sequence, a similar PCR strategy was used as described in Example 3. The template for PCR was JHE-KK. The PCR product was cloned into pCR-Script and sequenced as already described. An alternate pAcUW21 transfer vector was produced, pAcUW21-MCS6. In this vector, linkers were used to alter the unique cloning sites downstream of the p10 promoter such that the order of the Eco R1 and Bgl II sites was reversed. In addition, a unique Eco RV site was added to the vector between the Bgl II and Eco R1 sites.

The gel-purified PCR-derived fragment was cloned into JHE-KK linearized with Nco 1. This resulted in a construct in which the approximately 300 bp signal sequence minus PCR-derived insert was cloned in tandem downstream from the original 300 bp signal sequence positive 5' end. This construct was then digested with Eco R1 and Bgl II, and the appropriately sized JHE-KK lacking the signal sequence gel purified, then cloned into pAcUW21-MCS6. Recombinant virus was made and purified as described above, yielding "AcJHE-minus-KK."

EXAMPLE 6

JHE is N-glycosylated, with five potential glycosylation sites. Another JHE mutant was made, in which four of the five potential N-linked glycosylation sites, at positions 62, 161, 383, and 496 were removed by replacement of the asparagine residues, using site-directed mutagenesis. This mutant was designated as "JHE-4N," and it also does not have a 3'UTR. The virus expressing this mutant is referred to here as Ac.JHE-4N.

To make a signal sequence "minus" version of JHE-4N, a similar strategy was used as for the construction of JHE-minus-KK, with JHE-4N DNA as the PCR template. This virus is designated AcJHE-minus-4N.

In all cases, the pAcUW21 containing the signal sequence "minus" forms of JHE were sequenced before transfection.

EXAMPLE 7

T. ni "high 5" cells were grown in XL405 w/L-glutamine (JRH Biosciences, Woodland, Calif.), supplemented with 1% penicillin/streptomycin (Sigma, St. Louis, Mo.). Cells were grown at room temperature (approximately 25° C.), shaking at 130 rpm. For all experiments, cells were infected with the viruses at high MOI, when the cells were at a density of $1 \times 10^6$ cells/ml.

To establish enzyme expression levels for all six viruses over a time course of infection, cultures of cells were infected, and 5 ml aliquots were removed at 24, 48, 72, 96, and 120 hpi. These aliquots were frozen at −20° C. until JHE activity could be measured. These data were graphed, and from the plots, a time was chosen, roughly corresponding to the peak of expression, for subsequent experiments. For the JHE pair (by "pair" is meant with and without signal sequence) this was 96 hpi, for the JHE-KK pair, as well as the JHE-4N pair, this was 72 hpi.

To measure total JHE enzyme activity at the peak of expression for all six viruses, cells plus media was used. To determine cellular localization of the JHE activity, cells were spun down at 2000×g to give two fractions, cellular and extracellular (media). The cells were then broken in the presence of 1 mM EDTA by dounce homogenizer on ice. From this crude cell lysate, nuclei plus cell debris and cytoplasm were separated by spinning the cell lysate.

To measure protein expression levels at the peak of expression for all six viruses, the crude cell lysate was run on a SDS-PAGE gel, transferred to nylon membrane by standard procedures, probed using the JHE polyclonal antibody, and probed using the ECL Kit. Known quantities of purified JHE were run alongside for comparison.

Assay of JHE activity was done by the partition assay using [$^3$H]JH III as a substrate. No data were used which resulted from experiments outside conditions giving a linear dependence upon both time and protein concentration, all assays were done in triplicate. This extremely specific assay is useful in this context in that the [$^3$H]JH can readily enter cells; the cells are lysed upon addition to the trichloroethylene used to partition the aqueous and organic phases. Thus, this assay can measure the activity of JHE both inside and outside the cell, without an additional cell lysis step.

Two liters of T. ni "hi 5" cells were infected at high MOI with AcJHE-minus when they were at a concentration of $1 \times 10^6$ cells/ml. At three days post infection, cells were pelleted at 2000×g and washed extensively, then resuspended in 50 mM Tris-PO$_4$ pH 7.5, 20% glycerol, 1 mM EDTA, 1 mM β-mercaptoethanol, and 0.02% sodium azide. Cells were snap frozen in a dry ice/ethanol bath, and stored at −80° C. until use.

For purification, the cells were thawed and broken in a French Press at 14,000 cell pressure. The resulting fraction was centrifuged and the JHE purified by either affinity chromatography or classical ion exchange. The pure protein had the anticipated mobility on SDS-PAGE and IEF and the anticipated catalytic properites.

For all viruses, PIBs were obtained by feeding approximately 30 third instar H. virescens larvae diet contaminated with T. ni cells packed with polyhedra. Upon death, larvae were homogenized, and PIBs purified by differential centrifugation. Purified PIBs were resuspended in 60% Maltose=0.02% sodium azide, and sorted in aliquots, in glass, at −80° C. This procedure minimizes clumping. Immediately prior to use, an aliquot was diluted with dH$_2$O, and counted in a hemocytometer.

H. virescens eggs were obtained from Southern Insect Management Laboratory (USDA, Stoneville, Miss.) and reared on Tobacco Budworm Diet (BioServ, Frenchtown, N.J.) with the addition of 1.25 g/L streptomycin sulfate. For each virus, approximately 50 neonates were fed 2000 PIBs using a modified droplet feeding method. Mortality was monitored daily at 4, 6, or 8 hour intervals, according to the mortality rate. Assays were repeated three times. LT$_{50}$ values were determined.

H. virescens neonates were fed 2000 PIBs of either AcNPV (wild type virus containing no insert), AcJHE, or AcJHE-minus using a modified droplet feeding method. Control insects were fed droplets of dH$_2$O containing the dye used to monitor droplet uptake in the assay. Approximately 10 insects were used per treatment. At 72 hours post infection, insects were placed in an acidic extraction buffer consisting of 200 mM sodium acetate, pH 4.6, 5% sucrose, 1 mM EDTA, 0.01% phenylthiourea, and 0.02% sodium azide. Insects were ground in this buffer on ice, using a small pestle which fit well in the microfuge tubes. The crude whole insect homogenage was used to assay JHE enzyme activity by the modified partition assay.

Inspection of the JHE protein concentrations and enzyme activities of JHE produced in T. ni cell culture by the three matched pairs of viruses revealed that all of the viruses generated approximately the same amount of JHE enzyme activity at their peaks of expression. However, the time course of infection revealed that the AcJHE pair (with and without signal sequence) produced proteins showing a peak of enzyme activity a full 24 hours after the proteins produced by the other viruses.

EXAMPLE 8

The activity of the six viruses was then tested in insects. Since one of the major goals of producing genetically engineered baculoviruses is to obtain a virus with a faster rate of kill, these viruses were tested for time to death in neonates of H. virescens. They can be compared to wild type virus, AcNPV, and another recombinant baculovirus, AcNPV.AaIT, expressing a scorpion toxin. The LT$_{50}$ results obtained from triplicate bioassays are shown in Table 2.

TABLE 2

|  | LT$_{50}$ | SD | LRT$_{50}$ |
|---|---|---|---|
| AcMNPV.C6 | 102.70 | 5.68 | 1.00 |
| AcMNPV.AaIT | 79.76 | 5.89 | 0.78 |
| AcMNPV.JHE-wt(minus) | 91.63 | 7.22 | 0.89 |
| AcMNPV.JHE-4N(minus) | 96.85 | 5.18 | 0.94 |
| AcMNPV.JHE-KK(minus) | 101.63 | 2.91 | 0.98 |

Under these conditions, the three signal sequence "minus" viruses have very similar LT$_{50}$ values. From these results, we conclude that the signal sequence viruses, as a group, result in faster times to death than both AcNPV and AcJHE-KK, but slower than AcNPV.AaIT. The latter virus expresses the scorpion toxin AaIT under the control of the very late p10 promoter.

The results illustrate several points. First, the signal sequence "minus" viruses do not appear to produce more JHE protein than do the corresponding signal sequence positive viruses. In some cases, much less protein is produced by the signal sequence "minus" virus than its counterpart. The presence of a long 3'UTR in two of the mRNAs does not appear to have a great effect on the amount of protein produced. The proteins produced by the signal sequence "minus" viruses do appear to be intracellular and nonglycosylated, retaining enzyme activity. However, the JHE produced by these signal sequence "minus" viruses is much more effective in the insect in terms of speed of time to kill, as shown by the $LT_{50}$ results.

The foregoing examples illustrate certain embodiments of the present invention, and are not intended to limit the scope of the invention, which is defined in the appended claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2989 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
GAATTCCCAC  CGAACAGACA  TGACTTCACA  CGTACTCGCG  CTCGCCTTCC  TTCTACACGC    60

GTGCACAGCG  CTGGCGTGGC  AGGAGACAAA  TTCGCGCAGC  GTGGTCGCCC  ATCTGGACTC   120

CGGCATTATA  CGCGGCGTGC  CGCGCTCAGC  GGATGGCATC  AAGTTCGCCA  GCTTCCTAGG   180

AGTGCCCTAC  GCTAAGCAGC  CTGTTGGAGA  ACTCAGGTTT  AAGGAGCTCG  AGCCTCTAGA   240

ACCTTGGGAT  AAATATCCTGA ACGCAACAAA  TGAAGGACCC  ATCTGCTTCC  AAACAGATGT   300

ATTATACGGG  AGGCTCATGG  CGGCAAGCGA  GATGAGCGAG  GCTTGCATAT  ACGCCAACAT   360

TCATGTTCCA  TGGCAAAGCC  TTCCCCGAGT  GAGGGGGACC  ACACCTTTAC  GGCCTATCCT   420

GGTGTTCATA  CATGGTGGAG  GATTTGCTTT  CGGCTCCGGC  CACGAGGACC  TACACGGACC   480

AGAATATTTG  GTCACTAAGA  ATGTCATCGT  CATCACGTTT  AATTACAGAT  TGAACGTCTT   540

CGGTTTCCTG  TCCATGAACA  CAACAAAAAT  CCCCGGGAAT  GCCGGTCTCC  GGGATCAGGT   600

AACCCTGTTG  CGCTGGGTGC  AAAGGAACGC  CAAGAATTTC  GGAGGAGACC  CCAGCGACAT   660

CACCATAGCG  GGGCAGAGCG  CTGGTGCATC  AGCTGCGCAT  CTACTGACTC  TTTCTAAAGC   720

TACTGAAGGT  CTTTTCAAAA  GAGCGATTCT  GATGAGCGGA  ACAGGAATGA  GCTACTTCTT   780

TACTACTTCT  CCACTTTTCG  CGGCCTACAT  TTCGAAACAG  TTGTTGCAAA  TCCTGGGCAT   840

CAACGAGACG  GATCCCGAAG  AAATACATCG  GCAGCTCATC  GACCTACCCG  CAGAGAAACT   900

GAACGAGGCT  AACGCCGTCC  TGATTGAACA  AATTGGCCTG  ACAACCTTCC  TCCCTATTGT   960

GGAATCCCCA  CTACCTGGAG  TAACAACCAT  TATTGACGAT  GATCCAGAAA  TCTTAATAGC  1020

CGAAGGACGC  GGCAAGAATG  TTCCACTTTT  AATAGGATTT  ACCAGCTCAG  AATGCGAGAC  1080

TTTCCGCAAT  CGACTATTGA  ACTTTGATCT  CGTCAAAAAG  ATTCAGGACA  ATCCTACGAT  1140

CATAATACCG  CCTAAACTGT  TATTTATGAC  TCCACCAGAG  CTGTTGATGG  AATTAGCAAA  1200
```

-continued

| | | | | | | |
|---|---|---|---|---|---|---|
|GACTATCGAG|AGAAAGTACT|ACAACGGTAC|AATAAGTATC|GATAACTTCG|TAAAATCATG|1260|
|TTCAGATGGC|TTCTATGAAT|ACCCTGCATT|GAAACTGGCG|CAAAAACGTG|CCGAAACTGG|1320|
|TGGAGCTCCA|CTGTACTTGT|ACCGGTTCGC|GTACGAGGGT|CAGAACAGCA|TCATCAAGAA|1380|
|GGTAATGGGG|CTGAACCACG|AGGGTGTCGG|CCACATTGAG|GACTTAACCT|ATGTGTTTAA|1440|
|GGTCAACTCT|ATGTCCGAAG|CTCTGCACGC|ATCGCCTTCT|GAGAATGATG|TGAAAATGAA|1500|
|GAATCTAATG|ACGGGCTATT|TCTTAAATTT|TATAAAGTGC|AGTCAACCGA|CATGCGAAGA|1560|
|CAATAACTCA|TTGGAGGTGT|GGCCGGCTAA|CAACGGCATG|CAATACGAGG|ACATTGTGTC|1620|
|TCCCACCATC|ATCAGATCCA|AGGAGTTCGC|CTCCAGACAA|CAAGACATTA|TCGAGTTCTT|1680|
|CGACAGCTTC|ACCAGTAGAA|GCCCGCTTGA|ATGATAAGAC|TGAACTATTG|TCATCGATAT|1740|
|AAATATGTTG|TTAATGTTAG|TTAAGAGTTC|TCATAGTGCA|GTGAGCGTTT|GAACTGAACC|1800|
|ACTGGTCTCA|GAAGATCGAA|GTTTCATCCT|ATGACATAAG|AGTGTACAAT|GTTTCAGTT|1860|
|AAGTGTTGAT|GTTGATACTT|TAATTTGCAT|TAATTTATTT|AGAGTAAGGT|TAATGTCACA|1920|
|AGTCTAGTCG|GTTACTTAAG|TAATTTCTTG|CCAACATTGG|TGTAATGCCT|TTTCGTTGAG|1980|
|TTTCAAAAAA|TATTAATATT|ATATGCATTA|TAAATTAAAT|TCTAATTTTC|ATCGTAGAAT|2040|
|ATAATACCAT|AGTTAGCATT|GTTGCTCTTT|GAGAAGAGGT|CAATGCCCAG|CAATAGGAAA|2100|
|GTACAAAGGT|CGATGATGAT|GAATAAGCAG|ATAAATTATA|GAGCTTCTAC|TTCATTGATG|2160|
|TTGATTGAAA|CTCATGTTGA|CATCTTTGTG|AAATCATTTG|ACATCAAAGA|GAACATAACT|2220|
|TTAGTTTAAC|GACACGGATT|TACTATTAGG|AACAGCTAGA|CCTTCTTTAG|ACCTAGTATT|2280|
|GTTTTACGAA|GCAATTGTAA|TAAAACTTGG|GTGAAAATAA|AGGTTAGTCG|TAATTACAGC|2340|
|ATTACGACTA|AGCTTTGTTA|GTGCCCGGAA|GATTGATCTC|ATAAAACTAC|ACTAGGCTAT|2400|
|GGATAACAAT|CCGCCCGCAA|TTTAATTTTA|AGTTAATATA|AGTTATTTTG|AAAATTATAT|2460|
|TTTTGTACAA|AATGCTGCAG|ATCACGGGAC|GTCTATTCGA|TTTGATATTC|GAAAAGGAAT|2520|
|TTTACTATTT|TGACTTTCGA|GAGTCTGACG|AGATGTTAGT|ATATTCGCGA|GCATCCATAA|2580|
|ATCGAATTTG|TGTTAATTGG|AAGTTCGTTC|TCGATCTAGA|TTCGTAAGGT|GCATGGTGCT|2640|
|ACTTACTAGA|TAAATATTAG|CAATACAATT|GAATTTCGTA|TTCCAAAACT|ATCCCTATTC|2700|
|CTGATTACGA|AGGGCAGTGT|ACAAAATAGT|GAAAAATTGT|AATTGTACAG|AATGATAATC|2760|
|CCGTGATCCA|AGCACTCGAG|ATGCGTAATG|AAGCGACTGA|TGTAACGTAT|TATAATTTAA|2820|
|GTCAATTTAC|TATTAGTTTT|CAACGCCTTT|GTAAATATTT|CACTTTCTAA|TGTAATTTTA|2880|
|GTATTCCCGC|ACAATGACGC|CAGAGTACAA|TGATCGGACG|CGATCGCGTG|GCGTTACATT|2940|
|TAATGATTCA|AATAAATAAT|TGCGTCGGAC|GGACGTGAAA|AAAAAAAA| |2989|

( 2 ) INFORMATION FOR SEQ ID NO:2:

( i ) SEQUENCE CHARACTERISTICS:
        ( A ) LENGTH: 3047 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

| | | | | | | |
|---|---|---|---|---|---|---|
|GAATTCCAAC|AGACATGACT|TCACACGTAC|TCGCGCTCGC|CTTCTTTCTA|CACGCGTGCA|60|

-continued

```
CAGCGCTGGC GTGGCAGGAG ACAAATTCGC GCAGCGTGCT CGCCCATCTG GACTCCGGCA    120
TTATACGCGG CGTGCCGCGC TCAGCGGATG GCATCAAGTT CGCCAGCTTC CTAGGAGTGC    180
CCTACGCTAA GCAGCCTGTT GGAGAACTCA GGTTTAAGGA GCTCGAGCCT CTAGAACCTT    240
GGGATAATAT CCTGAACGCA ACAAATGAAG GACCCATCTG CTTCCAAACA GATGTATTAT    300
ACGGGAGGCT CATGGCGGCA AGCGAGATGA GCGAGGCTTG CATATACGCC AACATTCATG    360
TTCCATGGCA AAGCCTTCCC CGAGTGAGGG GGACCACACC TTTACGGCCT ATCCTGGTGT    420
TCATACATGG TGGAGGATTT GCGTTCGGCT CCGGCCACGA GGACCTACAC GGACCAGAAT    480
ATTTGGTCAC TAAGAATGTC ATCGTCATCA CGTTTAATTA CAGATTGAAC GTCTTCGGTT    540
TCCTGTCCAT GAACACAACA AAAATCCCCG GAATGCCGG TCTCCGGGAT CAGGTAACCC     600
TGTTGCGCTG GGTGCAAAGG AACGCCAAGA ATTCGGAGG AGACCCCAGC GACATCACCA     660
TAGCGGGGCA GAGCGCTGGT GCATCAGCTG CGCATCTACT GACTCTTTCT AAAGCTACTG    720
AAGGTCTTTT CAAAAGAGCG ATTCTGATGA GCGGAACAGG AATGAGCTAC TTCTTTACTA    780
CTTTCTCCAC TTTTCGCGGC CTACATTTCG AAACAGTTGT TGCAAATCCT GGGCATCAAC    840
GAGACGGATC CCCGAAGAAA TACATCGGCA GCTCATCGAC CTACCCGCCG AGAAACTGAA    900
CGAGGCTAAC GCCGTCCTGA TTGAACAAAT TGGCCTGACA ACCTTCGTCC CTATTGTGGA    960
ATCCCCACTA CCTGAAGTAA CAACCATTAT TGACGATGAT CCAGAAATCT AATAGCCGA    1020
AGGACGCGGC AAGAATATTC CACTTTTAAT AGGATTTACC AGCTCAGAAT GCGAGACTTT   1080
CCGCAATCGA CTATTGAACT TTGATCTCGT CAAAAAGATT CAGGACAATC CTACGATCAT   1140
AATACCGCCT AAACTGTTAT TTATGACTCC ACCAGAGCTG TTGATGGAAT TAGCAAAGAC   1200
TATCGAGAGA AAGTACTACA ACGGTACAAT AAGTATCGAT AACTTCGTAA ATCATGTTC    1260
AGATGGCTTC TATGAATACC CTGCATTGAA ACTGGCGCAA AAACGTGCCG AAACTGGTGG   1320
AGCTCCACTG TACTTGTACC GGTTCGCGTA CGAGGGTCAG AACAGCATCA TCAAGAAGGT   1380
AATGGGGCTG AACCACGAGG GTGCCGGCCA CATTGAGGAC TTAACCTACG TGTTTAAGGT   1440
CAACTCTATG TCCGAAGTTC TGCACGCATC GCCTTCTGAG AATGATGTGA AAATGAAGAA   1500
TCTAATGACG GGCTATTTCT TAAATTTTAT AAAGTGCAGT CAACCGACAT GCGAAGACAA   1560
TAACTCACTG GAGGTGTGGC CGGCTAACAA CGGCATGCAA TACGAGGACA TTGTGTCTCC   1620
CACCATCATC AGATCCAAGG AGTTCGCCTC CAGACAACAA GACATTATCG AGTTCTTCGA   1680
CAGCTTGTCC AGTAGAAGCC CACTTGAATG ATAAGACTGA ACTATTGTCA TCGATATAAA   1740
TATGTTGTTA ATGTTAGTTA AGAGTTCTCA TAGTGCAGTG AGCGTTTGAA CTGAACCACT   1800
GGTCTCAGAA GATCGAAGTT TCATCCTATG ACATAAGAGT GTACAATGTT TTCAGTTAAG   1860
TGTTGATGTT GATACTTTAA TTTGCATTAA TTTATTTAGA GTAAGGTTAA TGTCACAAGT   1920
CTAGTCGGTT ACTAAAGTAA TTTCTTGCCA ACATTGGTGT AATGCCTTTT CGTTGAGTTT   1980
CAAAAAATAT TATTATTATA TGCATTTTAA ATTAAATTCT AATTTTCATC GTAGAATACA   2040
ATACCATAGT TAGCATTGTT GCTCTTTGAG AAGAGGCCAA TGCCCAGCAA TAGGAAAGTA   2100
CAAAGGTCGA TGATGATGAA TAAGCAGATA AATTATAGAG CTTCTACTTC ATTGATATTG   2160
ATTGAAACTC ATGTTGACAT CTTTGTGAAA TCATTTGACA TCAAAGAGAA CATAACTTTA   2220
GTTAACGAC ACGGATTTAC TATTGAAACA GCTAGACCTT CTTTAGACCT AGTATTGTTT    2280
TACGAAGCAA TTGTAATAAA ACTTGGGTGA AAATAAAGGT TAGTCGTAAT TACAGCATTA   2340
CGACTAAGCT TTGTTAGTGC CCGGAAGATT GATCTCATAA AACTACACTA GGCTATGGAT   2400
AACAATCCGC CCGCAATTTA ATTTTAAGTT AATATAAGTT ATTTTGAAAA TTATATTTTT   2460
```

| | | | | | | |
|---|---|---|---|---|---|---|
|GTACAAAATG|CTGCAGATCA|CGGGACGTCT|ATTCGATTTG|ATATTCGAAA|AGGAATTTAA|2520|
|CTATTTTGAC|TTTCGAGAGT|CTGACGTGAT|GTTAGTATAT|TCGCGAGCAT|CCATAATTAA|2580|
|CTATTTTGAC|TTTCGAGAGT|CTGACGTGAT|GTTAGTATAT|TCGCGAGCAT|CCATAAATCG|2640|
|AATTTGTGTT|AATTGGAAGT|TCGTTCTCGA|TCTAGATTCG|TAAGGTGCAT|GGTGCTACTT|2700|
|ACTAGATAAA|TATTAGCAAT|ACAATTGAAT|TTCGTATTCC|AAACGAAGGG|CAGTGTACAA|2760|
|AATAGTGAAA|AATTGTAATT|GTACAGAATG|ATAATCCCGT|GATCCAAGCA|CTCGAGATGC|2820|
|GTAATGAAGC|GACTGATGTA|ACGTATTATA|ATTAAGTCA|ATTACTATT|AGTTTTCAAC|2880|
|GCCTTTGTAA|ATATTTCACT|TTCTAATGTA|ATTTAGTAT|TCCCGCACAA|TGACGCCGAG|2940|
|TACAATGATC|GGACGCGATC|GCGTGGCGTT|ACATTTAATG|ATTCAAATAA|ATAATTGCGT|3000|
|CGGACGGACG|TGGAAAAAAA|AAAAAAAAA|AAAAAAAAA|AAAAAA| |3047|

It is claimed:

1. A mutated nucleotide sequence having a sequence as in SEQ ID NO:1 or SEQ ID NO:2 but mutated therefrom, wherein said mutation is a deletion of a signal sequence, the mutated nucleotide sequence coding for a mutated juvenile hormone esterase.

2. The nucleotide sequence as in claim 1 wherein the mutated juvenile hormone esterase is missing about 19 N-terminus amino acid residues.

3. The nucleotide sequence as in claim 2 wherein the mutated juvenile hormone esterase further includes substitutions at lysine positions 29 and 522.

4. The nucleotide sequence as in claim 1 wherein the mutated juvenile hormone esterase further includes substitutions at asparagine positions 62, 161, 383, and 496.

5. A mutated nucleotide sequence having a sequence as in SEQ ID NO:1 or SEQ ID NO:2 but mutated therefrom, wherein said mutation codes for a substituted amino acid residue at one or more of asparagine positions 62, 161, 383, or 496, the mutated nucleotide sequence coding for a mutated juvenile hormone esterase.

6. An expression vector comprising in operable linkage the nucleotide sequence of claims 1–5, and a promoter which is heterologous to the nucleotide sequence, wherein the promoter regulates the transcription of the nucleotide sequence in a host cell.

7. The expression vector of claim 6 wherein the host cell is a noctuid insect cell.

8. The expression vector of claim 6 wherein the vector is derived from a baculovirus.

9. The expression vector of claim 8 wherein the baculovirus is *Autographa californica*.

10. The expression vector of claim 7 wherein the promoter is a polyhedrin, basic protein, or a p10 promoter.

11. A method of controlling insects comprising contacting an insect with a vector of claim 6, wherein the vector upon expression produces a mutated juvenile hormone esterase.

12. A method of controlling insects comprising contacting an insect with a vector of any one of claims 7–10, wherein the vector upon expression produces a mutated juvenile hormone esterase.

* * * * *

UNITED STATES PATENT AND TRADEMARK OFFICE
CERTIFICATE OF CORRECTION

PATENT NO. : 5,674,485
DATED : October 7, 1997
INVENTOR(S) : Bruce D. Hammock et al.

It is certified that error appears in the above-identified patent and that said Letters Patent is hereby corrected as shown below:

The Title Page, Related U.S. Application Data, [63] replace:
"[63] Continuation-in-part of Ser. No. 927,851, Aug. 10, 1992, abandoned, which is a continuation-in-part of Ser. No. 725,226, Jun. 26, 1991, abandoned, which is a continuation of Ser. No. 265,507, Nov. 1, 1988." with --[63] Continuation-in-part of Ser. No. 927,851, Aug. 10, 1992, U.S. Pat. No. 5,643,776, which is a continuation-in-part of Ser. No. 725,226, Jun. 26, 1991, abandoned, which is a continuation of Ser. No. 265,507, Nov. 1, 1988, abandoned.--

Column 8, Line 34 replace:
"(Langone and Yon Vunakis, eds.) 73, pp. 46-52, Academic" with --(Langone and Von Vunakis, eds.) 73, pp.46-52, Academic"

Column 11, Line 67 replace:
"asparagine residues, Asn 62, Asn 161, Asn 383 and Ash 496" with --asparagine residues, Asn 62, Asn 161, Asn 383 and Asn 496--

Col. 1, line 5, replace "1992, which" with --1992, now U.S. Pat. No. 5,643,776, which --.

Signed and Sealed this

Seventh Day of July, 1998

Attest:

BRUCE LEHMAN

*Attesting Officer*  *Commissioner of Patents and Trademarks*